(12) United States Patent
Parihar et al.

(10) Patent No.: US 9,526,516 B2
(45) Date of Patent: *Dec. 27, 2016

(54) DETACHABLE END EFFECTOR AND LOADER

(71) Applicant: Ethicon Endo-Surgery, Inc., Cincinnati, OH (US)

(72) Inventors: Shailendra K. Parihar, Mason, OH (US); Wells D. Haberstich, Loveland, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/840,779

(22) Filed: Aug. 31, 2015

(65) Prior Publication Data

US 2016/0022298 A1    Jan. 28, 2016

Related U.S. Application Data

(63) Continuation of application No. 13/627,177, filed on Sep. 26, 2012, now Pat. No. 9,125,681.

(51) Int. Cl.
| | |
|---|---|
| *A61B 17/00* | (2006.01) |
| *A61B 17/29* | (2006.01) |
| *A61B 17/28* | (2006.01) |

(52) U.S. Cl.
CPC ...... *A61B 17/29* (2013.01); *A61B 2017/00362* (2013.01); *A61B 2017/00473* (2013.01);
(Continued)

(58) Field of Classification Search
CPC . A61B 2017/2931; A61B 17/29; A61B 17/28; A61B 2017/00362; A61B 2017/2902; A61B 2017/00473; A61B 2017/2829
See application file for complete search history.

(56) References Cited

U.S. PATENT DOCUMENTS

| | | |
|---|---|---|
| 3,043,309 A | 7/1962 | McCarthy |
| 3,358,676 A | 12/1967 | Frei et al. |

(Continued)

FOREIGN PATENT DOCUMENTS

| | | |
|---|---|---|
| DE | 10149421 A1 | 4/2003 |
| JP | 2005-261734 A | 9/2005 |

(Continued)

OTHER PUBLICATIONS

Co-Owned U.S. Appl. No. 12/576,529, filed Oct. 9, 2009.
(Continued)

*Primary Examiner* — Gregory Anderson
*Assistant Examiner* — Son Dang

(57) ABSTRACT

A surgical device comprises an elongate shaft having an outer tube and an inner rod positioned in the outer tube. The outer tube and inner rod each comprise a distal end and a proximal end. An actuator is operably connected to the proximal ends of the outer tube and the inner rod. An end effector is adapted for in vivo attachment to and detachment from the elongate shaft. The end effector comprises an outer casing comprising a first detent mating feature adapted to engage the distal end of the outer tube; an inner shuttle axially moveable relative the outer casing, the shuttle comprising a second detent mating feature adapted to engage the distal end of the inner rod; and a pair of surgical jaws having an opened position and closed position dependant on the relative axial position of the shuttle and casing. A tubular loader is sized to receive the end effector, the tubular loader comprising third detent mating feature adapted engage end effector.

4 Claims, 5 Drawing Sheets

(52) U.S. Cl.
CPC ............. *A61B 2017/2829* (2013.01); *A61B 2017/2902* (2013.01); *A61B 2017/2931* (2013.01)

(56) References Cited

U.S. PATENT DOCUMENTS

| | | | |
|---|---|---|---|
| 3,710,399 A | 1/1973 | Hurst |
| 3,893,448 A | 7/1975 | Brantigan |
| 3,906,217 A | 9/1975 | Lackore |
| 3,988,535 A | 10/1976 | Hickman et al. |
| 4,047,136 A | 9/1977 | Satto |
| 4,063,561 A | 12/1977 | McKenna |
| 4,099,192 A | 7/1978 | Aizawa et al. |
| 4,278,077 A | 7/1981 | Mizumoto |
| 4,384,584 A | 5/1983 | Chen |
| 4,585,282 A | 4/1986 | Bosley |
| 4,597,390 A | 7/1986 | Mulhollan et al. |
| 4,655,746 A | 4/1987 | Daniels et al. |
| 5,052,402 A | 10/1991 | Bencini et al. |
| 5,053,043 A | 10/1991 | Gottesman et al. |
| 5,201,743 A | 4/1993 | Haber et al. |
| 5,282,806 A | 2/1994 | Haber et al. |
| 5,286,255 A | 2/1994 | Weber |
| 5,308,357 A | 5/1994 | Lichtman |
| 5,314,424 A | 5/1994 | Nicholas |
| 5,330,502 A | 7/1994 | Hassler et al. |
| 5,352,219 A | 10/1994 | Reddy |
| 5,392,917 A | 2/1995 | Alpern et al. |
| 5,417,203 A | 5/1995 | Tovey et al. |
| 5,441,059 A | 8/1995 | Dannan |
| 5,468,250 A | 11/1995 | Paraschac et al. |
| 5,502,698 A | 3/1996 | Mochizuki |
| 5,507,297 A | 4/1996 | Slater et al. |
| 5,507,774 A | 4/1996 | Holmes et al. |
| 5,540,648 A | 7/1996 | Yoon |
| 5,562,655 A | 10/1996 | Mittelstadt et al. |
| 5,578,052 A | 11/1996 | Koros et al. |
| 5,593,402 A | 1/1997 | Patrick |
| 5,613,937 A | 3/1997 | Garrison et al. |
| 5,618,303 A | 4/1997 | Marlow et al. |
| 5,632,764 A | 5/1997 | Beideman et al. |
| 5,716,326 A | 2/1998 | Dannan |
| 5,718,714 A | 2/1998 | Livneh |
| 5,722,988 A | 3/1998 | Weisshaupt |
| 5,762,255 A | 6/1998 | Chrisman et al. |
| 5,782,748 A | 7/1998 | Palmer et al. |
| 5,792,165 A | 8/1998 | Klieman et al. |
| 5,810,865 A | 9/1998 | Koscher et al. |
| 5,810,877 A | 9/1998 | Roth et al. |
| 5,881,615 A | 3/1999 | Dahl et al. |
| 5,893,875 A | 4/1999 | O'Connor et al. |
| 5,928,263 A | 7/1999 | Hoogeboom |
| 5,980,455 A | 11/1999 | Danie et al. |
| 6,024,748 A | 2/2000 | Manz et al. |
| 6,059,719 A | 5/2000 | Yamamot et al. |
| 6,099,537 A | 8/2000 | Suga et al. |
| 6,126,359 A | 10/2000 | Dittrich et al. |
| 6,159,200 A | 12/2000 | Verdur et al. |
| 6,273,882 B1 | 8/2001 | Whittier et al. |
| 6,309,397 B1 | 10/2001 | Julia et al. |
| 6,315,789 B1 | 11/2001 | Cragg |
| 6,419,688 B1 | 7/2002 | Bacher et al. |
| 6,471,172 B1 | 10/2002 | Lemke et al. |
| 6,589,211 B1 | 7/2003 | MacLeod |
| 6,595,984 B1 | 7/2003 | DeGuillebon |
| 6,626,824 B2 | 9/2003 | Ruegg et al. |
| 6,635,071 B2 | 10/2003 | Boche et al. |
| 6,663,641 B1 | 12/2003 | Kovac et al. |
| 6,666,875 B1 | 12/2003 | Sakurai et al. |
| 6,723,043 B2 | 4/2004 | Kleeman et al. |
| 6,770,081 B1 | 8/2004 | Cooper et al. |
| 6,776,165 B2 | 8/2004 | Jin |
| 6,814,742 B2 | 11/2004 | Kimura et al. |
| 6,827,712 B2 | 12/2004 | Tovey et al. |
| 6,860,878 B2 | 3/2005 | Brock |
| 6,869,395 B2 | 3/2005 | Page et al. |
| 6,884,213 B2 | 4/2005 | Raz et al. |
| 6,916,314 B2 | 7/2005 | Schneider et al. |
| 6,936,003 B2 | 8/2005 | Iddan |
| 6,942,674 B2 | 9/2005 | Belef et al. |
| 6,986,738 B2 | 1/2006 | Glukhovsky et al. |
| 6,994,708 B2 | 2/2006 | Manzo |
| 7,039,453 B2 | 5/2006 | Mullick et al. |
| 7,042,184 B2 | 5/2006 | Oleynikov et al. |
| 7,066,879 B2 | 6/2006 | Fowle et al. |
| 7,083,579 B2 | 8/2006 | Yokoi et al. |
| 7,122,028 B2 | 10/2006 | Looper et al. |
| 7,125,403 B2 | 10/2006 | Julian et al. |
| 7,169,104 B2 | 1/2007 | Ueda et al. |
| 7,199,545 B2 | 4/2007 | Oleynikov et al. |
| 7,211,094 B2 | 5/2007 | Gannoe et al. |
| 7,241,290 B2 | 7/2007 | Doyle et al. |
| 7,297,142 B2 | 11/2007 | Brock |
| 7,331,967 B2 | 2/2008 | Lee et al. |
| 7,429,259 B2 | 9/2008 | Cadeddu et al. |
| 7,448,993 B2 | 11/2008 | Yokoi et al. |
| 7,559,887 B2 | 7/2009 | Dannan |
| 7,566,331 B2 | 7/2009 | Looper et al. |
| 7,604,642 B2 | 10/2009 | Brock |
| 7,651,471 B2 | 1/2010 | Yokoi et al. |
| 7,666,181 B2 | 2/2010 | Abou El Kheir |
| 7,678,043 B2 | 3/2010 | Gilad |
| 7,691,103 B2 | 4/2010 | Fernandez et al. |
| 7,691,126 B2 | 4/2010 | Bacher |
| 7,699,835 B2 | 4/2010 | Lee et al. |
| 7,722,599 B2 | 5/2010 | Julian et al. |
| 7,841,980 B2 | 11/2010 | Minosawa et al. |
| 7,862,553 B2 | 1/2011 | Ewaschuk |
| 7,894,882 B2 | 2/2011 | Mullick et al. |
| 7,901,398 B2 | 3/2011 | Stanczak et al. |
| 8,012,154 B2 | 9/2011 | Livneh |
| 8,021,358 B2 | 9/2011 | Doyle et al. |
| 8,038,612 B2 | 10/2011 | Paz |
| 8,052,636 B2 | 11/2011 | Moll et al. |
| 8,057,502 B2 | 11/2011 | Maliglowka et al. |
| 8,088,062 B2 | 1/2012 | Zwolinski |
| 8,114,098 B2 | 2/2012 | Kimura et al. |
| 8,128,643 B2 | 3/2012 | Aranyi et al. |
| 8,133,254 B2 | 3/2012 | Dumbauld et al. |
| 8,182,414 B2 | 5/2012 | Handa et al. |
| 8,187,166 B2 | 5/2012 | Kuth et al. |
| 8,353,897 B2 | 1/2013 | Doyle et al. |
| 8,377,044 B2 | 2/2013 | Coe et al. |
| 8,397,335 B2 | 3/2013 | Gordin et al. |
| 8,398,544 B2 | 3/2013 | Altamirano |
| 8,409,076 B2 | 4/2013 | Pang et al. |
| 8,475,361 B2 | 7/2013 | Barlow et al. |
| 8,518,024 B2 | 8/2013 | Williams et al. |
| 8,545,519 B2 | 10/2013 | Aguirre et al. |
| 8,623,011 B2 | 1/2014 | Spivey |
| 8,636,648 B2 | 1/2014 | Gazdzinski |
| 8,721,529 B2 | 5/2014 | Hess et al. |
| 8,721,539 B2 | 5/2014 | Shohat et al. |
| 8,747,394 B2 | 6/2014 | Belson et al. |
| 8,758,391 B2 | 6/2014 | Swayze et al. |
| 8,764,735 B2 | 7/2014 | Coe et al. |
| 8,828,046 B2 | 9/2014 | Stefanchik et al. |
| 8,845,661 B2 | 9/2014 | D'Arcangelo et al. |
| 8,939,997 B2 | 1/2015 | Martinez et al. |
| 8,979,891 B2 | 3/2015 | McLawhorn et al. |
| 9,125,681 B2 | 9/2015 | Parihar et al. |
| 9,142,527 B2 | 9/2015 | Lee et al. |
| 9,186,203 B2 | 11/2015 | Spivey et al. |
| 2002/0128645 A1 | 9/2002 | Messerly |
| 2002/0177843 A1 | 11/2002 | Anderson et al. |
| 2003/0114731 A1 | 6/2003 | Cadeddu et al. |
| 2004/0093039 A1 | 5/2004 | Schumert |
| 2004/0152941 A1 | 8/2004 | Asmus et al. |
| 2004/0267254 A1 | 12/2004 | Manzo et al. |
| 2005/0033354 A1 | 2/2005 | Montalvo et al. |
| 2005/0119640 A1 | 6/2005 | Sverduk et al. |
| 2005/0131457 A1 | 6/2005 | Douglas et al. |
| 2005/0250984 A1 | 11/2005 | Lam et al. |
| 2005/0272972 A1 | 12/2005 | Iddan |

(56) References Cited

U.S. PATENT DOCUMENTS

| | | |
|---|---|---|
| 2005/0272974 A1 | 12/2005 | Iddan |
| 2005/0273139 A1 | 12/2005 | Krauss et al. |
| 2005/0288555 A1 | 12/2005 | Binmoeller |
| 2006/0079933 A1 | 4/2006 | Hushka et al. |
| 2006/0184161 A1 | 8/2006 | Maahs et al. |
| 2006/0190035 A1 | 8/2006 | Hushka et al. |
| 2006/0258905 A1 | 11/2006 | Kaji et al. |
| 2007/0010709 A1 | 1/2007 | Reinschke |
| 2007/0049966 A1 | 3/2007 | Bonadio et al. |
| 2007/0073247 A1 | 3/2007 | Ewaschuk |
| 2007/0123748 A1 | 5/2007 | Meglan |
| 2007/0270651 A1 | 11/2007 | Gilad et al. |
| 2008/0004656 A1 | 1/2008 | Livneh |
| 2008/0015413 A1 | 1/2008 | Barlow et al. |
| 2008/0142005 A1 | 6/2008 | Schnell |
| 2008/0154299 A1 | 6/2008 | Livneh |
| 2008/0242939 A1 | 10/2008 | Johnston |
| 2009/0171147 A1 | 7/2009 | Lee et al. |
| 2010/0198248 A1 | 8/2010 | Vakharia |
| 2010/0249700 A1 | 9/2010 | Spivey |
| 2011/0040322 A1 | 2/2011 | Major |
| 2011/0087224 A1 | 4/2011 | Cadeddu et al. |
| 2011/0087265 A1* | 4/2011 | Nobis .................... A61B 17/29 606/205 |
| 2011/0087266 A1 | 4/2011 | Conlon et al. |
| 2011/0115891 A1 | 5/2011 | Trusty et al. |
| 2011/0230869 A1 | 9/2011 | Altamirano |
| 2011/0288560 A1 | 11/2011 | Shohat et al. |
| 2012/0053402 A1 | 3/2012 | Conlon et al. |
| 2012/0053406 A1 | 3/2012 | Conlon et al. |
| 2012/0065627 A1 | 3/2012 | Ghabrial et al. |
| 2012/0078290 A1 | 3/2012 | Nobis et al. |
| 2012/0078291 A1 | 3/2012 | Nobis et al. |
| 2012/0083778 A1 | 4/2012 | McGaffigan et al. |
| 2012/0083826 A1 | 4/2012 | Chao et al. |
| 2012/0088965 A1 | 4/2012 | Stokes et al. |
| 2012/0089093 A1 | 4/2012 | Trusty et al. |
| 2012/0259325 A1 | 10/2012 | Houser et al. |
| 2012/0289773 A1 | 11/2012 | Joshi et al. |
| 2012/0316575 A1 | 12/2012 | Farin et al. |
| 2014/0005474 A1 | 1/2014 | Farin et al. |
| 2014/0066711 A1 | 3/2014 | Farin et al. |
| 2014/0088637 A1 | 3/2014 | Parihar et al. |
| 2014/0088638 A1 | 3/2014 | Parihar et al. |
| 2014/0243799 A1 | 8/2014 | Parihar et al. |
| 2014/0243800 A1 | 8/2014 | Parihar et al. |
| 2014/0243868 A1 | 8/2014 | Parihar et al. |
| 2014/0277018 A1 | 9/2014 | Parihar et al. |
| 2014/0378953 A1 | 12/2014 | Coe et al. |
| 2015/0088191 A1 | 3/2015 | Coe et al. |

FOREIGN PATENT DOCUMENTS

| | | | |
|---|---|---|---|
| JP | | 2005261734 A * | 9/2005 |
| WO | WO 2010/114634 A1 | | 10/2010 |
| WO | WO 2011/044353 A1 | | 4/2011 |
| WO | WO 2012/040183 A1 | | 3/2012 |
| WO | WO 2012/112622 A3 | | 8/2012 |
| WO | WO 2013/007764 A2 | | 1/2013 |
| WO | WO 2013/048963 A2 | | 4/2013 |
| WO | WO 2014/052177 A1 | | 4/2014 |

OTHER PUBLICATIONS

International Preliminary Report dated Mar. 5, 2013; International Application No. PCT/US2011/050198.
International Search Report dated Mar. 2, 2012; International Application No. PCT/US2011/050198.
International Preliminary Report dated Apr. 11, 2012; International Application No. PCT/US2010/051812.
International Search Report dated Mar. 21, 2011; International Application No. PCT/US2010/051812.
International Preliminary Report dated Mar. 26, 2013; International Application No. PCT/US2011/052327.
International Search Report dated Dec. 12, 2011; International Application No. PCT/US2011/052327.
International Preliminary Report dated Apr. 1, 2014; International Application No. PCT/US2012/056900.
International Search Report dated Apr. 3, 2013; International Application No. PCT/US2012/056900.
International Preliminary Report dated Sep. 1, 2015; International Application No. PCT/US2014/015738.
International Search Report dated May 28, 2014; International Application No. PCT/US2014/015738.
International Preliminary Report dated Mar. 31, 2015; International Application No. PCT/US2013/060803.
International Search Report dated Dec. 20, 2013; International Application No. PCT/US2013/060803.

* cited by examiner

DETACHABLE END EFFECTOR AND LOADER

BACKGROUND

The present invention relates in general to surgical devices and procedures, and more particularly to minimally invasive surgery.

Surgical procedures are often used to treat and cure a wide range of diseases, conditions, and injuries. Surgery often requires access to internal tissue through open surgical procedures or endoscopic surgical procedures. The term "endoscopic" refers to all types of minimally invasive surgical procedures including laparoscopic, arthroscopic, natural orifice intraluminal, and natural orifice transluminal procedures. Endoscopic surgery has numerous advantages compared to traditional open surgical procedures, including reduced trauma, faster recovery, reduced risk of infection, and reduced scarring. Endoscopic surgery is often performed with an insufflatory fluid present within the body cavity, such as carbon dioxide or saline, to provide adequate space to perform the intended surgical procedures. The insufflated cavity is generally under pressure and is sometimes referred to as being in a state of pneumoperitoneum. Surgical access devices are often used to facilitate surgical manipulation of internal tissue while maintaining pneumoperitoneum. For example, trocars are often used to provide a port through which endoscopic surgical instruments are passed. Trocars generally have an instrument seal, which prevents the insufflatory fluid from escaping while an instrument is positioned in the trocar.

While a variety of different minimally invasive surgical devices are known, no one has previously made or used the surgical devices and methods in accordance with the present invention.

SUMMARY

In one embodiment, a surgical device comprises an elongate shaft having an outer tube and an inner rod positioned in the outer tube. The outer tube and inner rod each comprise a distal end and a proximal end. An actuator is operably connected to the proximal ends of the outer tube and the inner rod. An end effector is adapted for in vivo attachment to and detachment from the elongate shaft. The end effector comprises an outer casing comprising a first detent mating feature adapted to engage the distal end of the outer tube; an inner shuttle axially moveable relative the outer casing, the shuttle comprising a second detent mating feature adapted to engage the distal end of the inner rod; and a pair of surgical jaws having an opened position and closed position dependant on the relative axial position of the shuttle and casing. A tubular loader is sized to receive the end effector, the tubular loader comprising third detent mating feature adapted engage end effector.

The first, second, and third detent mating features may have a threshold disengagement force $F_1$, $F_2$, and $F_3$, respectively, of the following relative magnitudes: $F_1 < F_3 < F_2$. The first detent mating feature may comprise a leaf spring on the outer casing adapted to engage a notch on the outer tube. The third detent mating feature may comprise a leaf spring on the tubular loader adapted to engage a notch on the outer casing. The second detent mating feature may comprise a pair of proximally oriented prongs, each having a medially oriented tooth adapted to engage a notch on the inner rod. The distal end of the outer tube may comprise a sloped surface adapted to engage and laterally spread the prongs thereby disengaging the teeth from the notch on the inner rod.

In another embodiment, a surgical device comprises an elongate shaft comprising an outer tube and an inner rod positioned in the outer tube, the outer tube and inner rod each comprising a distal end and a proximal end. An actuator is operably connected to the proximal ends of the outer tube and the inner rod. An end effector is adapted for in vivo attachment to and detachment from the elongate shaft. The end effector comprises an outer casing comprising a first mating feature adapted to engage the distal end of the outer tube; an inner shuttle axially moveable relative the outer casing, the shuttle comprising a second mating feature adapted to engage the distal end of the inner rod; and a pair of surgical jaws having an opened position and closed position dependant on the relative axial position of the shuttle and casing. The second mating feature comprises a pair of proximally oriented prongs, each having a medially oriented tooth adapted to engage a notch on the inner rod. The distal end of the outer tube comprises a sloped surface adapted to engage and laterally spread the prongs thereby disengaging the teeth from the notch on the inner rod. The first mating feature may comprise a detent mechanism.

In yet another embodiment, a surgical device comprises an elongate shaft comprising an outer tube and an inner rod positioned in the outer tube, the outer tube and inner rod each comprising a distal end and a proximal end. An actuator is operably connected to the proximal ends of the outer tube and the inner rod. An end effector is adapted for in vivo attachment to and detachment from the elongate shaft. The end effector comprises an outer casing and a means to attach the outer casing to the outer tube; an inner shuttle axially moveable relative the outer casing and a means to attach the shuttle to the inner rod; and a pair of surgical jaws having an opened position and closed position dependant on the relative axial position of the shuttle and casing. A tubular loader is sized to receive the end effector and includes a means to attach the end effector in the tubular loader.

BRIEF DESCRIPTION OF DRAWINGS

While the specification concludes with claims which particularly point out and distinctly claim the invention, it is believed the invention will be better understood from the following description taken in conjunction with the accompanying drawings illustrating some non-limiting examples of the invention. Unless otherwise indicated, the figures are not necessarily drawn to scale, but rather to illustrate the principles of the invention.

DETAILED DESCRIPTION

Figure 1:
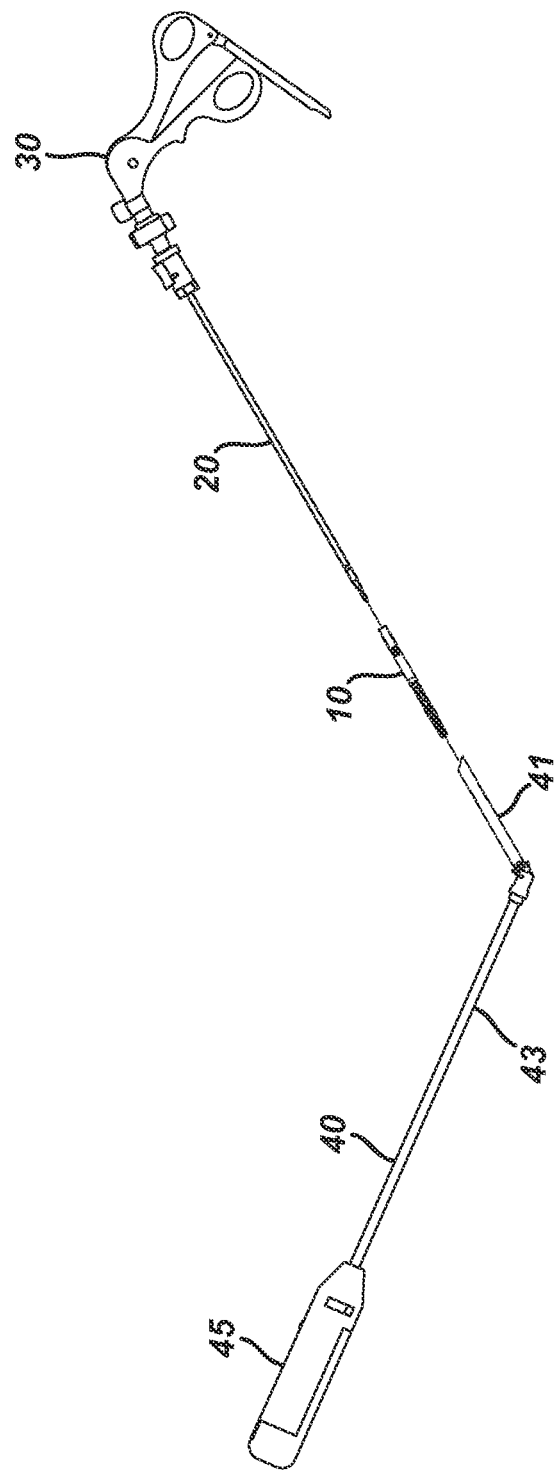
FIG. 1 depicts an example of a loader, end effector, shaft, and actuator.
Figure 2:
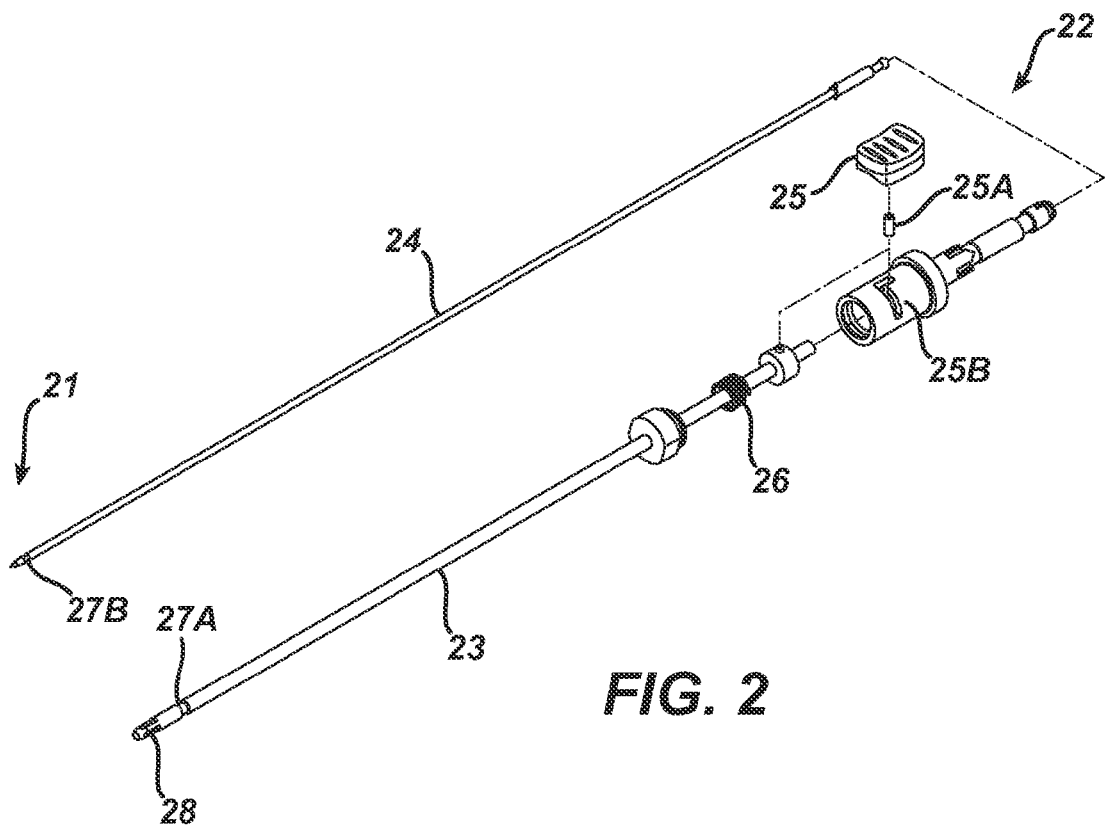
FIG. 2 depicts an exploded view of the shaft.
Figure 3:
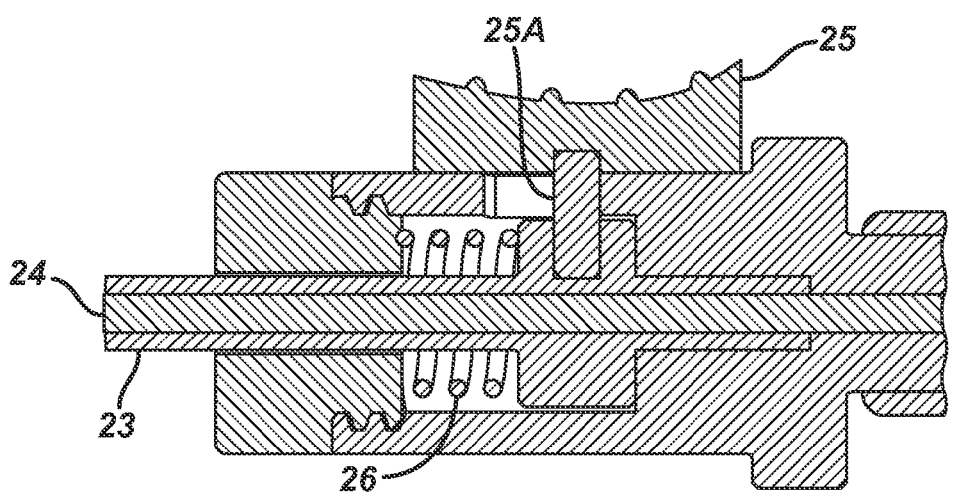
FIG. 3 depicts a cross-sectional view of a portion of the shaft.
Figure 4:
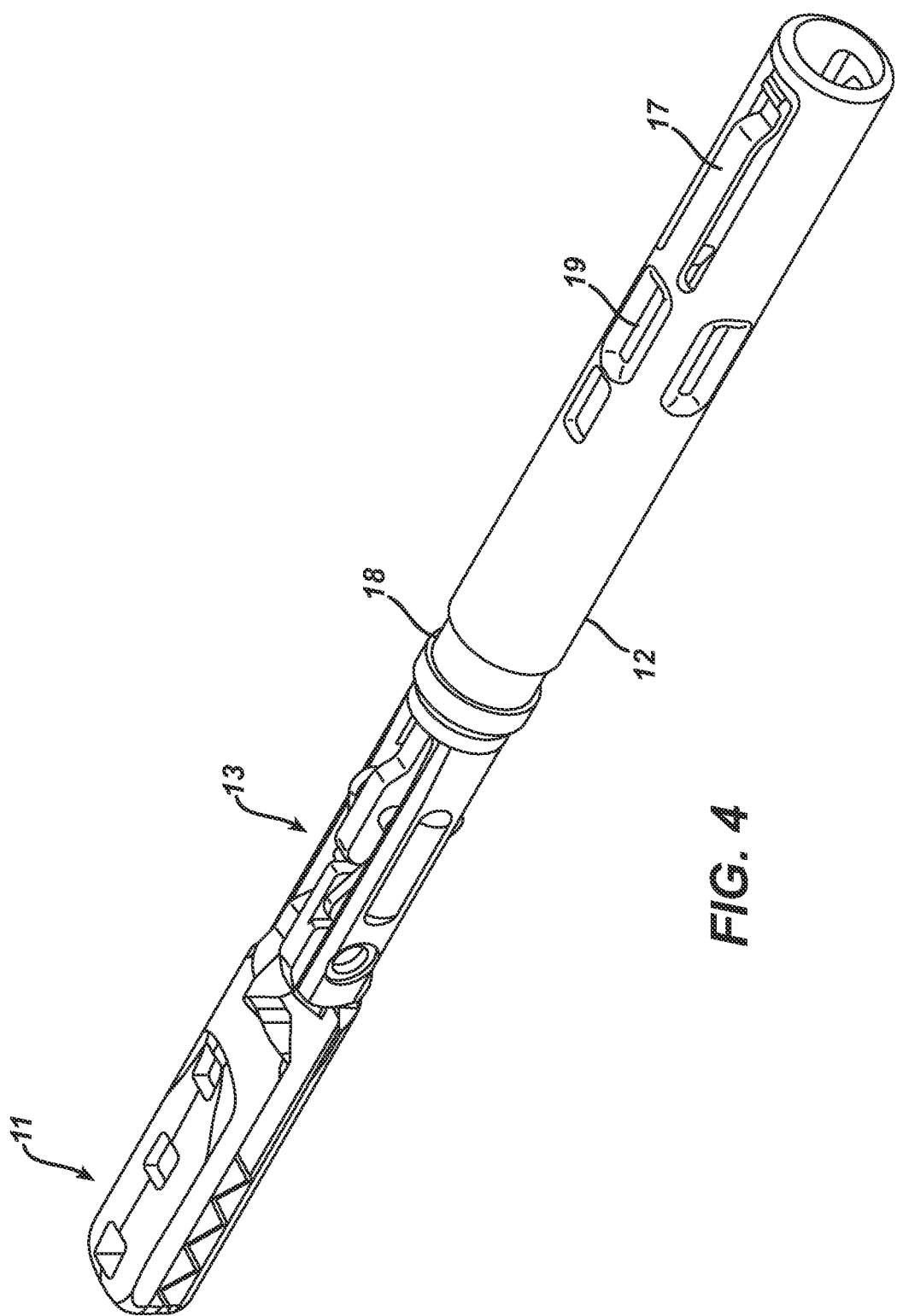
FIG. 4 depicts a perspective view of the end effector.
Figure 5:
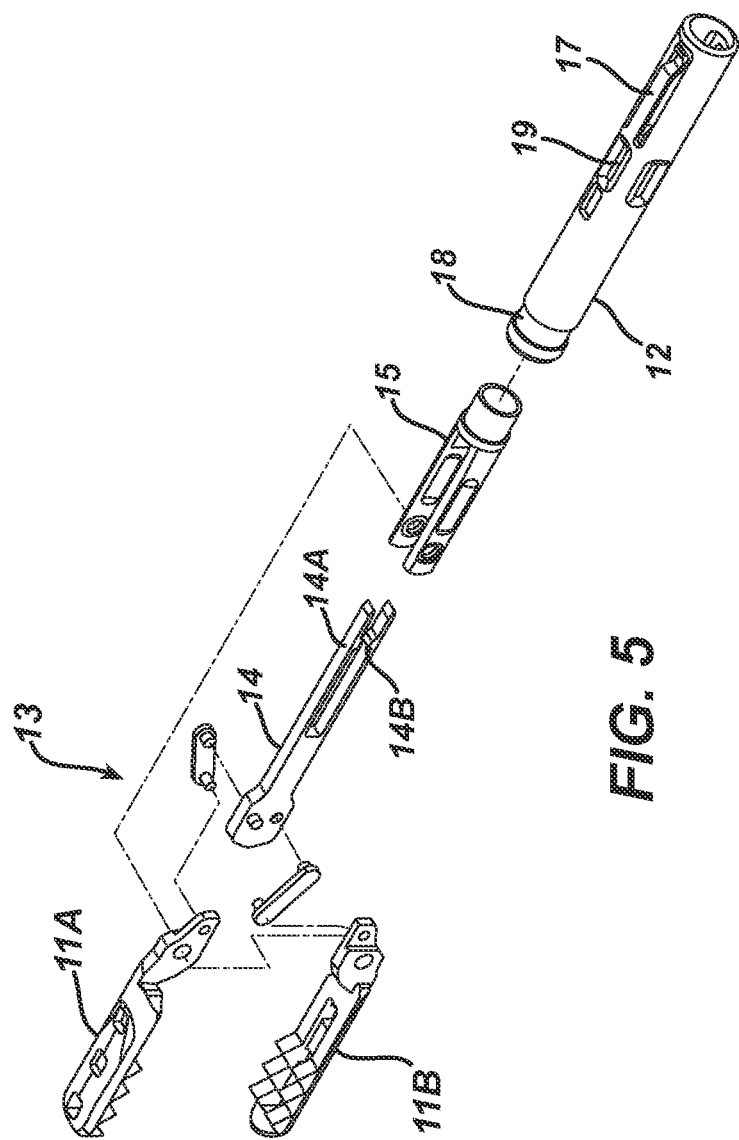
FIG. 5 depicts an exploded view of the end effector.
Figure 6:
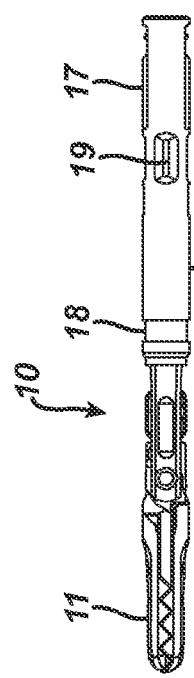
FIG. 6 depicts a side view of the loader and end effector.
Figure 7:
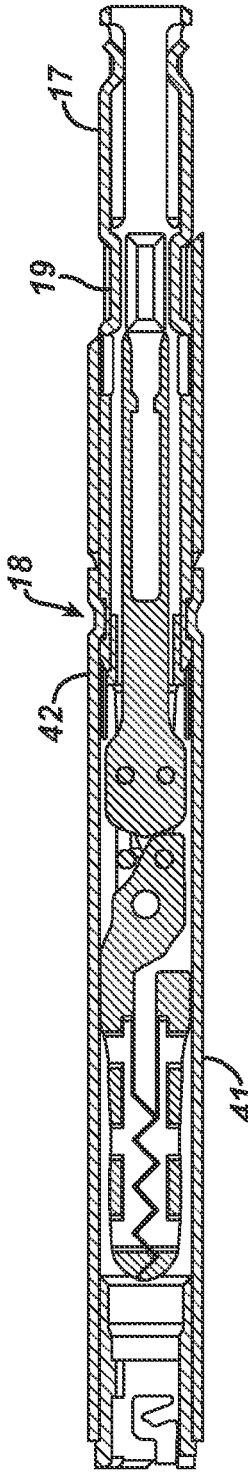
FIG. 7 depicts a cross-sectional view of the end effector locked in the loader.
Figure 8:
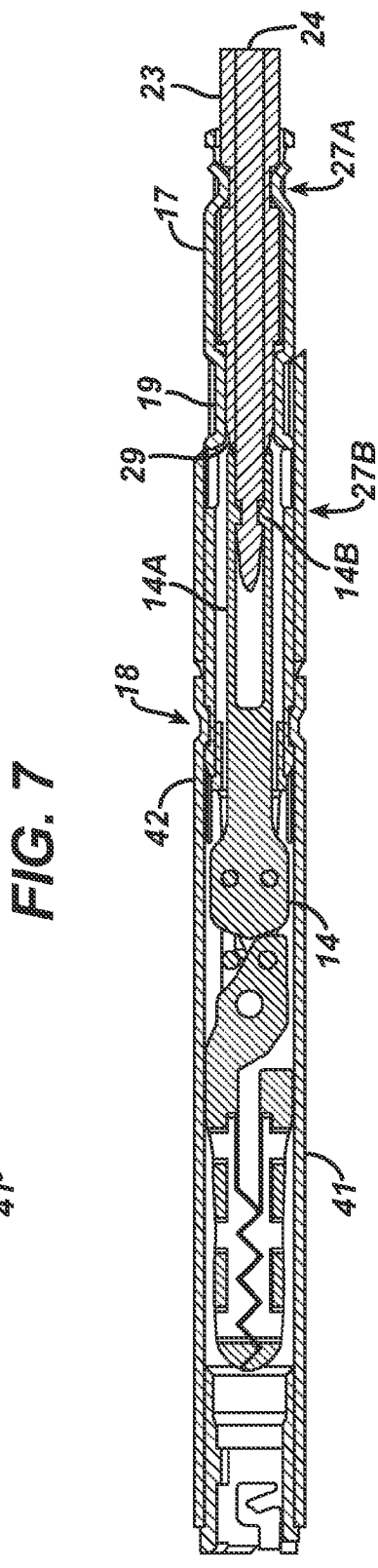
FIG. 8 depicts a cross-sectional view of the end effector attached to the shaft and unlocked in the loader.

The figures illustrate one example a laparoscopic surgical instrument system. The elongate shaft (20) comprises an outer tube (23) and an inner rod (24) positioned in the outer tube (23). The elongate shaft comprises a distal end (21) and a proximal end (22). The elongate shaft (20) may be rigid and adapted for insertion into a body cavity through an access device, such a trocar, or through direct percutaneous insertion without an access device. The elongate shaft (20) may also be flexible and sized for insertion through the working channel of a flexible endoscope. The rigid shaft embodiment is well suited for laparoscopic surgical procedures, and the flexible shaft embodiment is well suited for natural orifice intraluminal and natural orifice transluminal procedures.

An actuator (30) is operably connected to the proximal ends (22) of the outer tube (23) and the inner rod (24). The actuator (30) causes the inner rod (24) to move relative the outer tube (23). In this embodiment the actuator (30) is a manual pistol grip handle; however, a variety of other manual actuators could also be used, including a scissor grip handle, a syringe grip handle, endoscopic rotary knobs, and the like. The actuator (30) could also take the form of a robotic interface, such as an DAVINCI puck, a housing comprising gears or pulleys, servomechanisms, and the like.

The end effector (10) is adapted for in vivo attachment to and detachment from the elongate shaft (20). An inner shuttle (14) is axially moveable relative the outer casing (12). The shuttle comprises a mating feature adapted to attach to the distal end of the inner rod (24). The specific mating feature can vary, but in this embodiment the mating feature comprises a detent-type mechanism comprising a pair of proximally oriented prongs (14A), each functioning as leaf spring to bias a medially oriented tooth (14B) to engage the notch (27B) on the inner rod (24).

A pair of surgical jaws (11A, B) have an opened position and closed position dependant on the relative axial position of the shuttle (14) and the outer casing (12). A clevis (15) is fixed to the outer casing (12). A bar linkage mechanism (13) cooperates with the clevis (15) to translate the axial motion of the shuttle (14) to open and close the jaws (11); however, a variety of other known mechanisms can be used to effect operation of the jaws (11). In this embodiment, the jaws (11) are shown as a grasper; however, a variety of other tissue manipulating jaws could also be used, including dissectors, sheers, babcocks, forceps, staplers, clip appliers, and the like. Non-jawed end effectors could also be employed such as hook knives, snares, retractors, and the like. In the case of end effectors that require energy, appropriate energy transmission mechanisms known in the art can be added. For instance, appropriate electrical connections can be added between the shaft (20) and end effector (10) to enable bi-polar forceps. Similarly, an ultrasonic transducer and waveguide can be added for the ultrasonic shears end effector.

The end effector (10) comprises a mating feature (17) adapted to attach the outer casing (12) to the outer tube (23). In this embodiment the mating feature (17) is a detent-type mechanism comprising two leaf springs, positioned 180 degrees from each other on the outer casing (12), each having a medial facing tooth. As the outer tube (23) slides distally into the outer casing (12), and the leaf springs provide a biased snap-to-lock engagement of the teeth into the notch (27A). Other mating features could also be used, including threads, collets, bayonets, and the like. Keyway features (19) are sized and adapted to engage the spline features (28) on the outer tube (23) to facilitate rotational coupling when the outer tube (23) is attached to the outer casing (12).

A loader (40) comprises a handle (45), a shaft (43), and a distal tube (41) that may articulate relative the shaft (43). The tube (41) is sized to receive the end effector (10). The tube (41) comprises a mating feature (42) adapted to attach the end effector (10) inside the tube (41). In this embodiment the mating feature (42) is a detent-type mechanism comprising two leaf springs, positioned 180 degrees from each other on the tube (41), each having a medial facing tooth. As the end effector (10) slides into the tube (41), and the leaf springs provide a biased snap-to-lock engagement of the teeth into the notch (18). Other mating features could also be used, including threads, collets, bayonets, and the like.

The three mating features (17, 14A, and 42) each have a threshold axial force that will cause the respective components to disengage. For instance, the threshold disengagement force of the mating feature (17) is the axial force required to separate the outer housing (12) from the outer tube (23). Preferably, the relative magnitudes of the threshold disengagement forces are in accordance with the following equation:

$$F_1 < F_3 < F_2$$

where
$F_1$ is the threshold disengagement force between the outer housing (12) and the outer tube (23);
$F_2$ is the threshold disengagement force between the shuttle (14) and inner rod (24);
$F_3$ is the threshold disengagement force between the loader tube (41) and the end effector (10);

During surgery, the distal end (21) of the shaft (20) is inserted into the body cavity, such as the abdomen, pelvis, thorax, etc. The end effector (10) is attached into the tube (41) and also introduced into the body cavity, typically through an access port. The loader tube (41) can be articulated to facilitate bringing the end effector (10) into axial alignment with the shaft (20). The distal end (21) is then inserted into the end effector (10). The outer tube (23) slides distally into the outer casing (12) until the leaf springs of the mating feature (17) provide a biased snap-to-lock engagement into the notch (27A), thus attaching the outer casing (12) to the outer tube (23). The inner rod (24) slides distally into the shuttle (14) until the prongs (14A) provide a biased snap-to-lock engagement with the teeth (14B) into the notch (27B), thus attaching the shuttle (14) to the inner rod (24). The end effector (10) is now fully attached in vivo to the shaft (20) and can then be pulled from the tube (41). Because $F_2 > F_1$, pulling the shaft (20) proximally will cause the end effector (10) to be pulled out the loader tube (41). The loader (40) can be removed from the surgical field. Operation of the actuator (30) translates to operate the jaws (11), thus enabling a surgeon to manipulate tissue and perform minimally invasive surgical procedures.

In vivo detachment is achieved by reversing the attachment steps outlined in the previous paragraph. The loader (40) is introduced into the body cavity and the end effector (10) is slid into the tube (41). The distal end (21) of the outer tube (23) comprises a sloped surface (29). When the slider (25) is advanced distally and compresses the spring (26), the sloped surface (29) also advances distally to engage and laterally spread the shuttle prongs (14A) thus disengaging the teeth (14B) from the notch (27B) on the inner rod (24). The pin (25A) slides in L-shaped slot, enabling the surgeon to keep the sloped surface (29) in its distal-most position. The inner rod (24) can now be pulled from the shuttle (14), effectively making $F_2$ equal to zero (the sloped surfaces (29) may also be used to facilitate in vivo insertion of the inner rod (24) into the shuttle (14)). Because $F_3 > F_2$, pulling the shaft (20) proximally will cause the end effector (10) to detach from the inner rod (24) leaving the end effector (10) attached inside the loader tube (41).

Having shown and described various embodiments and examples of the present invention, further adaptations of the methods and devices described herein can be accomplished by appropriate modifications by one of ordinary skill in the art without departing from the scope of the present invention. Several of such potential modifications have been mentioned, and others will be apparent to those skilled in the art. For instance, the specific materials, dimensions, and the scale of drawings will be understood to be non-limiting examples. Accordingly, the scope of the present invention should be considered in terms of the following claims and is understood not to be limited to the details of structure, materials, or acts shown and described in the specification and drawings.

The invention claimed is:

1. A surgical device, comprising:
   a) an elongate shaft comprising an outer tube and an inner rod positioned in the outer tube, the outer tube and inner rod each comprising a distal end and a proximal end;
   b) an actuator operably connected to the proximal ends of the outer tube and the inner rod;
   c) an end effector adapted for in vivo attachment to and detachment from the elongate shaft, the end effector comprising:
      i) an outer casing comprising a first detent mating feature adapted to engage the distal end of the outer tube;
      ii) an inner shuttle axially moveable relative the outer casing, the shuttle comprising a second detent mating feature adapted to engage the distal end of the inner rod;
      iii) a pair of surgical jaws having an opened position and closed position dependant on the relative axial position of the shuttle and casing;
   d) a tubular loader sized to receive the end effector, the tubular loader comprising third detent mating feature adapted engage end effector;
   wherein the first, second, and third detent mating features have a threshold disengagement force F1, F2, and F3, respectively, of the following relative magnitudes:

$F1<F3<F2$.

2. The surgical device of claim 1, wherein the first detent mating feature comprises a leaf spring on the outer casing adapted to engage a notch on the outer tube.

3. The surgical device of claim 1, wherein the third detent mating feature comprises a leaf spring on the tubular loader adapted to engage a notch on the outer casing.

4. A surgical device, comprising:
   a) an elongate shaft comprising an outer tube and an inner rod positioned in the outer tube, the outer tube and inner rod each comprising a distal end and a proximal end;
   b) an actuator operably connected to the proximal ends of the outer tube and the inner rod;
   c) an end effector adapted for in vivo attachment to and detachment from the elongate shaft, the end effector comprising:
      i) an outer casing and a means to attach the outer casing to the outer tube;
      ii) an inner shuttle axially moveable relative the outer casing and a means to attach the shuttle to the inner rod;
      iii) a pair of surgical jaws having an opened position and closed position dependant on the relative axial position of the shuttle and casing;
   d) a tubular loader sized to receive the end effector and a means to attach the end effector in the tubular loader;
   wherein the means to attach the outer casing to the outer tube has threshold disengagement force F1, the means to attach the shuttle to the inner rod has threshold disengagement force F2, and the means to attach the end effector in the tubular loader has threshold disengagement force F3, and wherein $F1<F3<F2$.

* * * * *